United States Patent [19]
Yu et al.

[11] Patent Number: 6,077,872
[45] Date of Patent: Jun. 20, 2000

[54] USE OF CALCIUM L-THREONATE IN PREVENTING, INHIBITING AND CURING OSTEOPOROSIS AND RICKETS

[75] Inventors: Kai Yu; Zhiwen Wang; Fuping Kou, all of Beijing, China

[73] Assignee: Beijing Jueng Asia Pacific Life Scientific Research Center, Beijing, China

[21] Appl. No.: 09/199,694

[22] Filed: Nov. 25, 1998

[30] Foreign Application Priority Data

Jul. 8, 1998 [CN] China ................................ 98 1 15457

[51] Int. Cl.[7] .................................................. A01N 33/02
[52] U.S. Cl. ............................................ 514/663; 514/671
[58] Field of Search ....................................... 514/663, 671

[56] References Cited

U.S. PATENT DOCUMENTS 5,070,085 12/1991 Markham .................................. 514/161

OTHER PUBLICATIONS

Boutsen et al., "Primary Prevention of Glucocorticoid–Induced Osteoporosis with Intermittent Intravenous Pamidronate: A Randomized Trial", Caleif Tissue Int 61:266–271, 1997.

Luengo et al., "Prevention of Further Bone Mass Loss by Nasal Calcitonin in Patients on Long Term Glucocorticoid Therapy for Asthma: A Two Year Follow–Up Study", Thorax 49:1099–1102, 1994.

Okonofua et al., "Rickets in Nigerian Children: A Consequence of Calcium Malnutrition", Metabolism 40:209–213, 1991.

Recker et al., "Effect of Estrogens and Calcium Carbonate on Bone Loss in Postmenopausal Women", Annals of Internal Medicine 87:649–655, 1977.

*Primary Examiner*—Theodore J. Criares
*Attorney, Agent, or Firm*—Fish & Richardson P.C.

[57] ABSTRACT

The present invention relates to the use of calcium L-threonate, namely, to a method for preventing, inhibiting and curing osteoporosis and rickets using calcium L-threonate.

4 Claims, 2 Drawing Sheets

The enhancement of serum Ca level at various time after the administration ($\bar{X}\pm SD$)

Fig. 1

The enhancement of serum Ca level at various time after the administration ($\bar{X}\pm SD$)

Fig. 2 serum Ca level at various time after administration

Fig. 3

USE OF CALCIUM L-THREONATE IN PREVENTING, INHIBITING AND CURING OSTEOPOROSIS AND RICKETS

The present invention relates to the use of calcium L-threonate, particularly to the use of calcium L-threonate in preventing, inhibiting and curing osteoporosis and rickets.

Osteoporosis is a common metabolic bone disease. About ninety percent of osteoporosis is primary even though it may be caused by a number of other diseases. With the age increasing or menopause, the mineral substances and matrix of bone decrease which results in a change of the microstructure of bone tissues and thus deviates the normal loading functions of bones and markedly increases the risk of fracture and also brings about systematic bone pain and changes of body attitude.

The exact cause of primary osteoporosis is not clear at present, but it is generally the co-interaction result of a number of factors and links. Most scholars regard that the occurrence of osteoporosis is associated with various factors such as increased age, decreased hormone level and calcium dysbolism, etc. As for women, particularly for menopausal women, many researchers believe that the occurrence of osteoporosis is related to their decreased estrogens and calcium dysbolism. The occurrence of osteoporosis in the aged men is also resulted from multiple factors. Like estrogens, androgens of the aged men also participate in the process of bone metabolism and play important roles in bone formation and maintenance of bone amount. The protein assimilation of androgens promotes the synthesis of collagen which provides positions for the precipitation of calcium and phosphorus. In addition, increased secretion of parathormone in the aged men reduces the bone formation but enhances the bone absorption. The kidney degeneration (kidney weakness) in the aged men will reduce the activity of hydroxylase activating vitamin D, decrease the calcium intestinal absorption and result in negative calcium balance and loss of bone matrix. A lot of attempts have been done to treat osteoporosis with a variety of pharmacological agents, such as estrogens. Owing to the complexity of the causes of osteoporosis, there is evidence to show that some therapies (such as oral administration of calcium carbonate) are not effective for preventing osteoporosis (see Recker et al, *Annals of Int. Med.*, Vol. 87,6, pp 649–655,1977). Therefore, a more effective method of preventing and inhibiting osteoporosis is desirable.

Baby malacosteon or rickets is another common disease. However, at present, known therapeutic methods for this disease are disadvantageous and known calcium preparations or supplements for malacosteon or rickets are not quite effective, for example, as a most commonly used medicament, calcium carbonate preparation has some disadvantages such as that it can be absorbed poorly while consuming too much gastric acid and possibly damaging gastric mucosa. These methods have more limitations when applied to babies. So people have been longing for a more effective means of preventing, inhibiting or curing rickets.

It is an object of the present invention to provide a new application of calcium L-threonate. Particularly, the invention relates to the use of calcium L-threonate in preventing and inhibiting osteoporosis, malacosteon and rickets, or in curing rickets.

It is another object of the present invention to provide a method of preventing, inhibiting or curing osteoporosis and rickets.

In order to overcome the above disadvantages in the prior art, the inventors of the present invention have done extensive tests and clinical research and found that the object of preventing, inhibiting or curing osteoporosis and rickets can be achieved by orally administering calcium L-threonate which produces a net increase of bone matrix and thus enhances the bone density and bone mechanical property.

The calcium L-threonate used in the present invention is white powder, scarcely with odor, it can be solved in water but not in alcohol, ether and chloroform and has a formula $C_8H_{14}O_{10}Ca$ and a chemical structure represented by:

The compound can be prepared by: a certain amount of L-ascorbic acid (Vc) was added to water and solved, then calcium carbonate was slowly added into the mixture with stirring. To the above mixture, hydrogen peroxide was added dropwise at a temperature between 10° C. and 60° C. and maintained the temperature for 1–4 hours at 40–80° C. After active charcoal being added, the mixture was filtered. The filtrate was concentrated at a temperature between 30° C. and 90° C. and crystallized at ambient temperature. The crystal was dried at a temperature of 50–100° C.

In the above process of preparing calcium L-threonate, the addition of calcium carbonate must be carried out very slowly to avoid that the content rushed out of the container due to the dash of the produced carbon dioxide gas.

The above process of preparing calcium L-threonate may further comprises the operation of washing the cake obtained by filtering the mixture that had been treated with active charcoal, twice with hot water of 80° C. and the operation of concentrating the combined washes and filtrate.

The above process of preparing calcium L-threonate is advantageous for its reasonable procedure, simple operation, good yield as high as 90% and high purity of product. You may refer to Chinese Patent No. 1143464 for specific embodiment.

The calcium L-threonate according to the present invention may also be prepared by known methods in the prior art.

The calcium L-threonate according to the present invention can be administered orally.

The calcium L-threonate of the present invention can be used in various forms of formulations such as tablets, capsules and other forms of pharmaceutically acceptable compositions.

The pharmaceutical composition according to the present invention contains a certain amount of calcium L-threonate as (active) functional ingredient, along with a pharmaceutically acceptable carrier. The said carrier can be various carriers that have been widely employed in medicaments in the prior art such as excipients. The pharmaceutical composition of the present invention can be prepared by known methods in the prior art such as mixing, pelleting, tabletting.

The pharmaceutical composition according to the present invention may also contain other optional ingredients that can be used in pharmacology, for example, perfumes, colorants, sweets, etc. The preferred pharmaceutical composition of the present invention contains at least 60 percent, preferably at least 80 percent, more preferably at least 90 percent of calcium L-threonate along with other excipients and optional components as make-ups.

The pharmaceutical composition according to the present invention may also be used as food additives. It can be added into various foods as a food additive such as various drinks, solid food as bread or biscuit, and condiments as gourmet powder.

The dose of calcium L-threonate may vary with different recipients such as an adult or a baby. In all cases, the dose for an adult (60 kg body weight) falls between 12 g and 0.5 g each day, preferably falls between 10.7 g and 2 g each day such as a dose of 3.6 g/day, most preferably falls between 7 g and 3 g each day such as a dose of 3 g/day, corresponding to a dose of 1.4 g element calcium/day, 0.9 g element calcium /day, 0.45 g element calcium/day respectively on the basis of element calcium. For babies, the dose may be discounted according to their weights.

Figure 1:
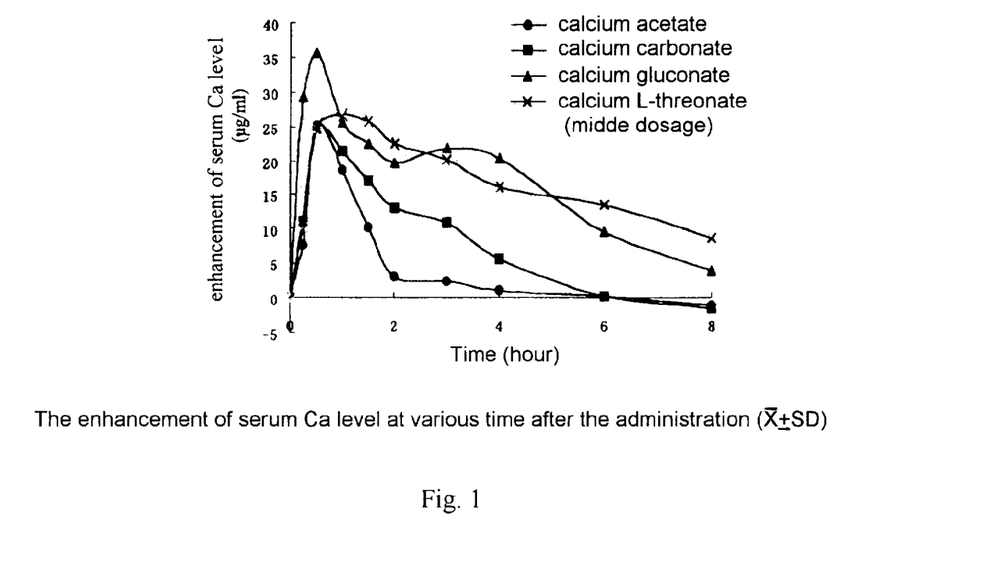
FIG. 1 shows the enhancement of serum Ca level at various time after the administration of agents.

In the present invention, we have studied the metabolic mechanism on the changes of calcium L-threonate in animal bodies versus time, pharmacokinetics parameters and the drainage of calciuria. All these studies demonstrated that the absorption metabolism of calcium L-threonate in rat intestine satisfied the One-Chamber model. The absorption of calcium L-threonate was relatively slower but more complete, the peak of serum calcium concentration arrived more late (its $T_{max}$=0.79 hrs), its half-life was longer ($T_{1/2}$=4.45 hrs) than those of other calcium agents such as calcium gluconate, calcium acetate, calcium carbonate. Calcium L-threonate can stay in serum for a longer time at a higher level. The area under the curve (AUC) equals to 191.75 $\mu$g/ml.hr (see FIG. 1). It is demonstrated that calcium L-threonate has a longer metabolic time and a higher bioavailability, which are beneficial for the balance between bone Ca and blood Ca to shift to the formation of bone Ca. This brings about a net increase of bone matrix and realizes the object to prevent osteoporosis. The kinetic change of the calcium L-threonate levels in the serum of house-hold dogs and pharmaceutical dynamic parameters thereof are consistent with those of rats. The specific content is included in the following Test I on pharmacokinetics of calcium L-threonate.

In the present invention, we have also tested the preventive effect of calcium L-threonate on osteoporosis of gelded female rats and male rats, and rickets of baby rats. The result was compared with that of Caltrate-D calcium carbonate +$V_D$).

In a test of rats osteoporosis model induced by feeding ovary-excised rats low-calcium diet, calcium L-threonate raised significantly the serum Ca level, decreased the serum ATP level and Tr-ACP level, enhanced the bone density, net weight, ash weight and the Ca content increased the femur strength (P) and the work expressed by energy (S) for enduring fracturing force, and also improved the calcification (K) and tenacity (Y) of bone. In comparison with Caltrate-D, calcium L-threonate can retard the loss of bone matrix. Calcium L-threonate is useful for preventing women from osteoporosis, especially useful for preventing menopaused women from osteoporosis. You can refer to Test II thereafter for details.

In the present invention, the study on male rats also showed the preventive and inhibitory effects of calcium L-threonate on osteoporosis. Therefore, calcium L-threonate can be used as basic medicament for curing and preventing the aged men from osteoporosis. You can refer to Test III thereafter for details.

In the present invention, the study on weanling baby rats indicated that calcium L-threonate can effectively control the loss of bone matrix, prevent and inhibit the occurrence of rickets.

In the present invention, we have also studied clinically the beneficial effect of calcium L-threonate on the bone density of preschool children and the therapeutic effect of calcium L-threonate on baby rickets.

The result of clinic research on the beneficial effect of calcium L-threonate on the bone mineral density of preschool children indicated that groups I and II having been administered calcium L-threonate for 1.5 months and 3 months respectively have higher BMDs than the calcium carbonate group and the blank control group. In the groups having been administered calcium L-threonate for 1.5 months and 3 months respectively, about 12% and 72% of the children have normal BMDs correspondingly. In contrast, only I sixth of the children in the calcium carbonate group have normal BMDs even after 3 months. This demonstrated that calcium L-threonate can increase the BMD of preschool children much more effectively than calcium carbonate.

In the present invention, forty rickets-baby at the age of from 3-month to 10-month are divided into two groups and are tested comparatively on the therapeutic effects of calcium L-threonate and calcium carbonate in the same dosage (300 mg element calcium). The results showed that the therapeutic effect of calcium L-threonate on baby rickets was significantly superior to that of calcium carbonate. So, calcium L-threonate can be used in preventing and curing baby rickets (see Test VI).

Calcium L-threonate of the present invention is useful for preventing people whose Ca absorption is deficient from osteoporosis, malacosteon and rickets. The recipients may be a child, an adolescent, or particularly the aged such as an aged man or a menopausal woman.

The calcium L-threonate of the present invention is useful for controlling the development of osteoporosis, malacosteon and rickets of patients such as a baby, an adolescent or an aged person as a menopausal woman suffered from osteoporosis, malacosteon and rickets.

Test I Pharmacokinetic Test of Calcium L-threonate
1. Agents

Calcium L-threonate, a white powder in crystalline containing 13% of calcium, was provided by Beijing Juneng Asia-Pacific Life Science Research Center. It was formulated with 0.5% CMC into solutions which have a calcium concentration of 15 mg/ml, 10 mg/ml and 5 mg/ml respectively. Calcium acetate, a white powder in crystalline of AR grade containing 25.3% of calcium, was formulated with 0.5% CMC into a mixed suspension which has a calcium concentration of 10 mg/ml. Calcium gluconate, a white powder in crystalline containing 8.9% of calcium, was produced by the Third Pharmaceuticals Factory of Harbin, China. It was formulated with 0.5% CMC into a mixed suspension which has a calcium concentration of 10 mg/ml. Calcium carbonate, a white powder of AR grade containing 40% of calcium, was formulated with 0.5% CMC into a mixed suspension which has a calcium concentration of 10 mg/ml.

2. Animals and apparatus (1) animals: Wistar rats of male and female each weighing 150–180 g, 180–220 g respectively, were provided by Department of Laboratory Animals, Beijing Medical University. Ordinary male crossbred domestic dogs each weighing 20.5–26.5 kg, were provided by Tongli Laboratory Animals Feed-Lot of Haidian District, Beijing.

(2) apparatus: Model WFX-1B Spectrophotometer of Atomic Absorption was produced by The Second Optical Apparatus Factory of Beijing, 83114; P-E 3030 Spectrophotometer of Atomic Absorption was produced by Perkin-Elmer Corp.,USA;DT-100 Single-Pan Balance ($1/10^4$) was produced by Beijing Optical Apparatus Factory; TJ-6 Centrifuge was produced by Beckman, USA; Model MVS-1 Vortex Mixer was produced by Beijing Beide Scientific Apparatus and Materials Co. Ltd.

3. Dosage and administration.

The administration route by pouring into the stomach is similar to clinical administration route. The dosage administered to rats is designed as the following six groups: the calcium L-threonate group in a high dosage of 2.31 g/kg body weight (containing 300 mg calcium/kg body weight), the calcium L-threonate group in a middle dosage of 1.54 g/kg body weight (containing 200 mg calcium/kg body weight), the calcium L-threonate group in a low dosage of 0.77 g/kg body weight (containing 100 mg calcium/kg body weight), the calcium acetate group in a dosage of 0.79 g/kg body weight (containing 200 mg calcium/kg body weight), the calcium gluconate group in a dosage of 2.25 g/kg body weight (containing 200 mg calcium/kg body weight) and the calcium carbonate group in a dosage of 0.50 g/kg body weight (containing 200 mg calcium/kg body weight). The dosage of calcium L-threonate for dogs is 1.54 g/kg body weight (containing 200 mg calcium/kg body weight) in correspondence with that of the middle dosage group of rats.

4. Test (1) Determination of pharmacokinetic parameters

Thirty Wistar rats are randomly divided into six groups: the calcium L-threonate group of high dosage, the calcium L-threonate group of middle dosage, the calcium L-threonate group of low dosage, the calcium acetate group, the calcium gluconate group and the calcium carbonate group. Twelve hours after the animals had been fasted, 0.5 mL plasma was sampled by excising eyeballs. The plasma was established as the blank group. Then rats were administered agents once in an amount of 20 mL/kg body weight by pouring into the stomach. 0.5 mL plasma was sampled by taking from eyeballs 0.25,0.5,1,1.5,2,3,4,6,8,12 and 16 hours later after the administration. The plasma was left for 30 minutes at room temperature and was then centrifuged at 300 rpm for 20 minutes. 0.2 mL serum was sampled, diluted to 2 mL with lanthanum diluent and homogenized. The concentration of calcium was measured by a Model WFX-1B Spectrophotometer of Atomic Absorption.

(2) Measurement of calcium L-threonate level in dog serum

Three domestic dogs were administered agents once in an amount of 200 mL/kg body weight by pouring into the stomach. 0.5 mL blood was sampled respectively from femur vein 0.5, 1, 2, 3, 4, 6, 8, 12, 16 and 24 hours later after the administration. The blood was left for 30 minutes at room temperature and was then centrifuged at 3000 rpm for 20 minutes. 0.2 mL serum was sampled, diluted to 2 mL with lanthanum diluent and homogenized. The solution is stored for measurement.

Figure 2:
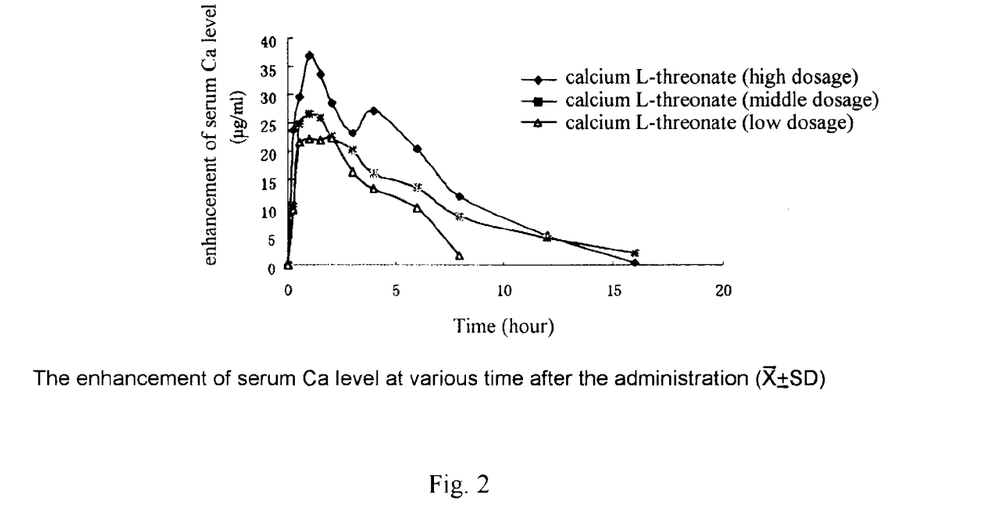
FIG. 2 shows the enhancement of serum Ca level at various time after the administration of agents.

5. Results (1) Parmacokinetic parameters (i) The enhancement of serum Ca level at various time after the administration of agents was shown in Table I and FIGS. 1 and 2.

TABLE I

The enhancement of serum Ca level at various time after the administration($X \pm SD$)

| group | the enhancement of serum Ca level($\mu g/ml$) | | | | | | | | | | |
|---|---|---|---|---|---|---|---|---|---|---|---|
| | 0.25 hrs | 0.5 hrs | 1 hrs | 1.5 hrs | 2 hrs | 3 hrs | 4 hrs | 6 hrs | 8 hrs | 12 hrs | 16 hrs |
| high dosage of calcium L-threonate | 23.7 ± 3.8 | 29.7 ± 5.7 | 36.8 ± 1.8 | 33.5 ± 2.4 | 28.6 ± 3.2 | 23.3 ± 7.4 | 27.1 ± 6.7 | 20.3 ± 7.7 | 12.2 ± 8.0 | 5.4 ± 2.7 | 0.5 ± 0.4 |
| middle dosage of calcium L-threonate | 10.3 ± 1.5 | 24.8 ± 7.3 | 26.6 ± 9.2 | 25.9 ± 3.3 | 22.5 ± 3.6 | 20.1 ± 2.4 | 16.2 ± 3.2 | 13.6 ± 3.7 | 8.7 ± 4.3 | 4.9 ± 1.5 | 2.1 ± 0.8 |
| low dosage of calcium L-threonate | 9.8 ± 0.5 | 21.5 ± 3.4 | 22.2 ± 2.7 | 21.8 ± 3.5 | 22.4 ± 3.5 | 16.4 ± 3.1 | 13.4 ± 2.6 | 10.1 ± 1.7 | 1.8 ± 1.5 | / | / |
| calcium acetate | 7.6 ± 3.9 | 25.1 ± 8.1 | 18.7 ± 2.7 | 10.3 ± 5.6 | 3.1 ± 2.9 | 2.4 ± 2.7 | 1.2 ± 2.7 | 0.3 ± 1.5 | −1.1 ± 1.3 | / | / |
| calcium carbonate | 11.1 ± 6.1 | 24.7 ± 7.2 | 21.4 ± 7.5 | 17.1 ± 8.0 | 13.2 ± 6.3 | 10.9 ± 7.3 | 5.7 ± 4.7 | 0.2 ± 0.9 | −1.4 ± 1.3 | / | / |
| calcium gluconate | 29.2 ± 6.0 | 35.7 ± 5.8 | 25.6 ± 5.1 | 22.6 ± 8.7 | 19.6 ± 4.9 | 21.8 ± 9.2 | 20.3 ± 8.1 | 9.6 ± 5.5 | 3.9 ± 4.0 | / | / |

(ii) The experimental data was fitted by computer with Software 3P87, and the following pharmacokinetics parameters was obtained: the absorption rate constant $k_a$=6.14 $hr^{-1}$, half-life of clearance $T_{1/2}$=4.45 hr, rate of clearance CL/F(S)=1.04 mg/kg/hr ($\mu g/ml$), apparent distributive volume V/F(c)=6.69 mg/kg ($\mu g/ml$), area under the curve AUC=191.75 ($\mu g/ml$).hr, maximum value of serum Ca $C_{max}$=27.17 $\mu g/ml$, time for arriving the maximum $T_{max}$=0.797 hr.

TABLE 2

Pharmacokinetics parameters of different calcium preparations

| Group | $k_a$(l/hr) | $T_{1/2}$(hr) | AUC ($\mu g/ml$).hr | $C_{max}$($\mu g/ml$) | $T_{max}$(hr) |
|---|---|---|---|---|---|
| middle dosage of calcium L-threonate | 6.14 | 4.45 | 191.75 | 27.17 | 0.79 |
| calcium acetate | 2.53 | 0.30 | 28.21 | 24.92 | 0.61 |
| calcium carbonate | 2.13 | 0.34 | 40.39 | 31.07 | 0.66 |
| calcium gluconate | 8.04 | 2.66 | 138.13 | 32.07 | 0.44 |

Figure 3:
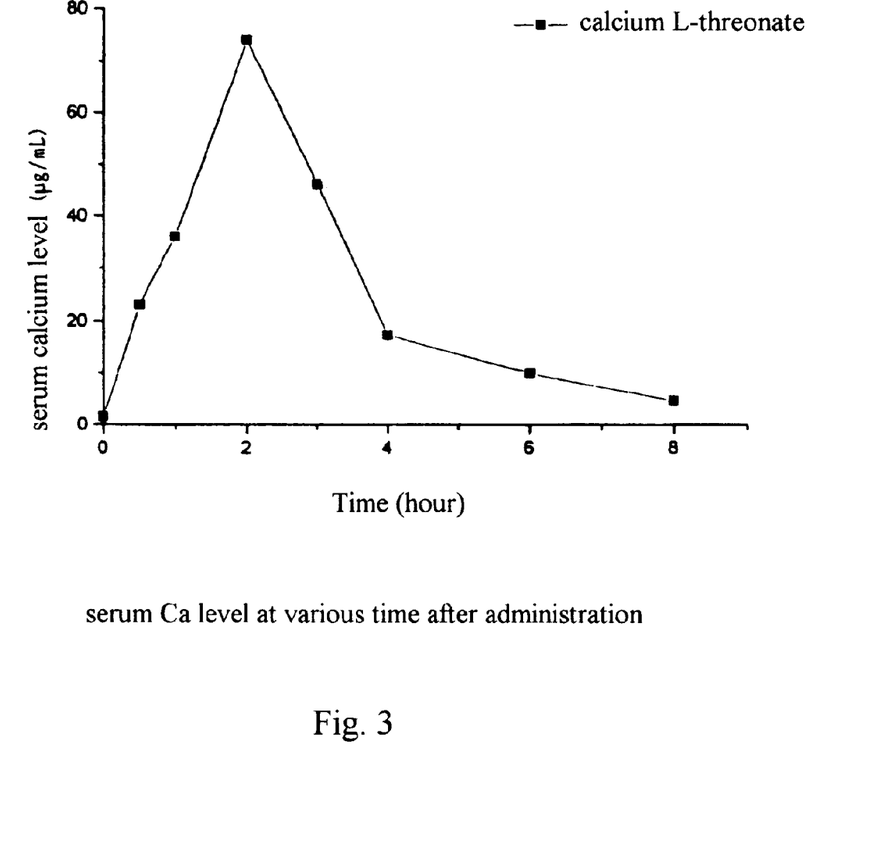
FIG. 3 shows serum Ca levels of dog at various time after administration of calcium L-threonate.

(2) measurement of calcium L-threonate level in the serum of dog and computation of pharmacokinetics parameters Serum Ca levels at various time after administration were shown in Table 3 and FIG. 3, the pharmacokinetics parameters fitted were listed in Table 4.

TABLE 3

| | Serum Ca levels at various time after administration($X \pm SD$) | | | | | | | | | |
|---|---|---|---|---|---|---|---|---|---|---|
| before administration | serum Ca levels after administration($\mu g/ml$) | | | | | | | | | |
| | 0.5 hrs | 1 hrs | 2 hrs | 3 hrs | 4 hrs | 6 hrs | 8 hrs | 12 hrs | 16 hrs | 24 hrs |
| $1.58 \pm 0.03$ | $23.11 \pm 2.68$ | $35.88 \pm 4.41$ | $74.04 \pm 0.50$ | $46.03 \pm 6.08$ | $17.24 \pm 3.72$ | $9.99 \pm 1.55$ | $4.66 \pm 2.52$ | $2.80 \pm 2.09$ | $4.30 \pm 1.83$ | $3.99 \pm 2.74$ |

TABLE 4

Pharmacokinetics parameters of calcium L-threonate in dog body

| $k_a$(l/hr) | $T_{1/2}$(hr) | AUC($\mu$g/ml).hr | $C_{max}$($\mu$g/ml) | $T_{max}$(hr) |
|---|---|---|---|---|
| 5.24 | 3.57 | 232.24 | 50.20 | 1.21 | n = 3

Test II. Study of the Preventing Effect of Calcium L-Threonate on Ovariectomy-Induced in Female Rats 1. Chemicals, Materials and Apparatus (1) The tested calcium L-threonate containing 13% of element calcium (white powder) was provided by Beijing Juneng Asia Pacific Life Science Research Center. Caltrate-D (positive control) with a calcium content of 600 mg Ca/tablet and 125 IU Vitamin D is available from Suzhou Lederle Sino-ATerica Pharmaceutical Co., Ltd.

(2) Animals and their breeding: Male Wistar rats at the age of 3 months were provided by Animal Center of the National Institute for the Identification of Pharmaceuticals and Biological Products, Beijing. The rats were fed low-calcium diet and offered with deionized water under conditions of room temperature (22±1° C.), relative humidity 40–60%, 12 hours of light/dark cycles.

(3) Pure synthetic low-calcium diet was formulated by mixing 40% fine wheat flour, 40% maize flour, 10% tyroprotein, 5% peanut oil, 3% AIN-76 mixed salts, 1% AIN-76 mixed vitamins, 1% cellulose and 0.3% DL-methionine, in which the calcium salt in AIN-76 mixed salts was replaced by glucose, and this preparation contains 64 mg calcium/100 g.

(4) Apparatus: Model BMD400G1 Bone Mineral Density Measuring Apparatus was produced by Institute of Beijing Broadcasting Technology, the National Atomic Energy Academy, China. Model WD-1 Electron Universal Test Machine was produced by The Trial Plant of Non-Metals, Changchun. The Ca, P and AKP in serum were measured by an Automatic Biochemical Analyzer.

2. Methods (1) Preparation of ovariotomized osteoporosis model

Female rats at the age of 3 months were excised of bilateral ovaries under sterilized condition, and were then fed low-calcium diet and offered with deionized water for 75 days, thus made an osteoporosis model.

(2) Treatment of Experiment Materials

Female 3-month-aged rats which had been excised of bilateral ovaries under sterilized condition were fed for a week until their wound was cured. Seventy healthy rats were selected and divided randomly into five groups of 14 rats. The first group was fed high dosage of calcium L-threonate 2.3 $\mu$g/kg/d, containing 300 mg element calcium/kg/d), the second group was fed middle dosage of calcium L-threonate (1.54 g/kg/d, containing 200 mg element calcium/kg/d), the third group was fed low dosage of calcium L-threonate (0.77 g/kg/d, containing 100 mg element calcium/kg/d), the fourth group was fed Caltrate-D in a dosage of 300 mg element calcium/kg/d, the fifth group was fed only deionized water every day and was established as model group, the sixth group (established as pseudo-surgery group) was fed normal diet. Group 1–5 were administered one time per day and 6 times per week and were also fed low-calcium diet and de-ionized water. The test period was 75 days. When the test was finished, rats were killed by bleeding from bilateral thigh arteries, the separated serum was used for measurement of biochemical parameters such as Ca, P, and AKP and Tr-ACP levels in serum. The bilateral femurs of rats were stripped off and stored in refrigerator. After the measurement of the bone mineral density, the left femur was stored for analysis of biomechanical characteristics. The right femur was stored for analysis of Ca content in femur.

(3) Measurement of serum Ca, P, AKP and Tr-ACP

Serum Ca, P and AKP were measured by a 4010 Automatic Biochemical Analyzer. Serum Ca was determined by calorimetric method using methylthymol blue. Serum P was determined by Mono-Reagent Method. Alkaline phosphatase was determined by method of disodium p-nitrophenylphosphonate (AKP) The tartaric-resistant acidic phosphatase (Tr-ACP) mineral was determined by Piedra procedure. All above reagent-box were available from the Clinical Chemicals Sub-plant of Beijing Chemical Plant.

(4) Measurement of bone mineral density. Fresh femur iced in refrigerator was measured of bone mineral content at the center (F50) and the proximal position 20% (F20) of femur by single photon absorptiometry (Model BMD400GI) with a scanning speed of 0.25 mm/s and a precision degree of 99%, the Apparatus was proofread using a standard apparatus provided by Jishuitan Hospital, Beijing. The data was processed by software used clinically. The bone mineral content was expressed by a unit of bone mineral content per square centimeter (BMC/cm$^2$).

(5) Measurement of femur bio-mechanical parameters

Three-point bending test was done on the fresh femur iced in refrigerator with a Model WD-1 Electron Universal Test Machine under the following conditions: a span of 2.5 cm, a 25 kg sensor (⅕₀), a speed of 2 mm/minute. The function of load versus flexibility was recorded by a finction recorder, wherein P represented the maximum of force at yielding point, Y was flexibility indicating the tenacity of materials. K, as the rate of slope, was a rigidity parameter of materials and was associated with the degree of calcification in bone mechanics. S stood for the work to yield or break femur.

(6) Measurement of dry weight, ash weight and calcium content of femur

After pulled off soft tissue, the right femur was dried for 5 hours in oven at the temperature of 120° C. until its weight kept a constant (dry weight), then the product was baked for 6 hours in muffle furnace at the temperature of 800° C. until the weight of the product kept a constant which was the ash weight, namely the total amount of inorganic salts. After part of the ash was resolved in dilute hydrochloride, the calcium content of ash was measured by the method of EDTA titration. All data was expressed as X±SD(n). The significance of differences between groups were assessed using the "T-test" method of two groups of small specimen.

3. Results (1) Ca, P, AKP, Tr-ACP in serum

The test result in Table V showed that the serum calcium level of rats in model group was markedly lower than that in normal-control group (P<0.01). This demonstrated that feeding the ovariectomized rats low-calcium diet long-time could result in the low serum calcium disease while feeding the ovariectomized rats calcium L-threonate long-time may prevent and inhibit the occurrence of the same disease and markedly raise the serum calcium level. There was significant difference between the two groups. The serum P level of model group rats was much higher than that of the normal-control group, but there was no evidence that calcium L-threonate or Caltrate-D could markedly affect the blood P level.

TABLE V

The effect of calcium L-threonate on the Ca, P levels in serum of ovariectomized rats(X ± SD)

| Group | serum Ca(mmol/L) | serum P(mmol/L) |
|---|---|---|
| calcium L-threonate | | |
| high dosage group | 2.30 ± 0.75** | 1.88 ± 0.58 |
| middle dosage group | 2.35 ± 0.35** | 1.87 ± 0.58 |
| low dosage group | 1.60 ± 0.75 | 2.08 ± 0.66 |
| Caltrate-D group | 2.07 ± 0.82** | 1.81 ± 0.28 |
| model-control group | 1.40 ± 0.72 | 1.91 ± 0.34 |
| normal-control group | 2.12 ± 0.75* | 1.63 ± 0.20 | note: n = 14, in comparison with model group **P < 0.01, *P < 0.05.

TABLE VI

The effect of calcium L-threonate on the AKP, Tr-ACP levels in serum of ovariectomized rats with osteoporosis

| Group | serum AKP (in Bessey-Loury unit) (U/L) | serum Tr-ACP (in Bessey-Loury unit) (U/L) |
|---|---|---|
| calcium L-threonate | | |
| high dosage group | 38.2 ± 10* | 7.2 ± 2.1 |
| middle dosage group | 41.4 ± 14* | 7.9 ± 2.4 |
| low dosage group | 48.7 ± 8.0 | 8.8 ± 1.8 |
| Caltrate-D group | 44.2 ± 12 | 7.4 ± 1.6 |

TABLE VI-continued

The effect of calcium L-threonate on the AKP, Tr-ACP levels in serum of ovariectomized rats with osteoporosis

| Group | serum AKP (in Bessey-Loury unit) (U/L) | serum Tr-ACP (in Bessey-Loury unit) (U/L) |
|---|---|---|
| model-control group | 50.3 ± 15 | 8.4 ± 2.8 |
| normal-control group | 38.7 ± 10* | 6.3 ± 2.0** | note: n = 14, in comparison with model group **P < 0.01, *P < 0.05.

The alkaline phosphatase in serum originates from an enzyme in osteoblast. When the bone reformation is flourishing, the enzyme's activity increases. The tartaric-resistant acidic phosphatase (Tr-ACP) in serum originates mainly from bone. It is an enzyme existing in osteoclast. When the resorption of bone enhances, the osteoclast in bone increases which results in the increase of Tr-ACP in serum. Table VI showed that the AKP and Tr-ACP levels in serum of model-control group rats were significantly higher than those of the normal-control group rats, this demonstrated that feeding the ovariectomized rats low-calcium diet chronically could result in the regeneration of bone and increased resorption of bone while feeding the ovariectomized rats calcium L-threonate chronically might decrease the AKP and Tr-ACP levels in serum, thus prevent and inhibit the resorption of bone.

(2) bone density, dry femur weight, ash weight and calcium content

Table VII showed that the bone density of rats feeding only calcium L-threonate chronically was markedly higher than that of model-control group rats. It was also found a good relationship between the effect of calcium L-threonate on the bone mineral density and dosages.

TABLE VII

The effect of calcium L-threonate on the bone density of ovariectomized rats with osteoporosis(X ± SD)

| Group | F50(BMC/BW) | F20(BMC/BW) |
|---|---|---|
| calcium L-threonate | | |
| high dosage group | 0.297 ± 0.021*** | 0.314 ± 0.020*** |
| middle dosage group | 0.282 ± 0.020 | 0.315 ± 0.032** |
| low dosage group | 0.289 ± 0.021* | 0.288 ± 0.021** |
| Caltrate-D group | 0.275 ± 0.013 | 0.282 ± 0.021* |
| model-control group | 0.274 ± 0.017 | 0.256 ± 0.022 |
| model-control group | 0.280 ± 0.016* | 0.307 ± 0.024*** | note: in comparison with model group *P < 0.001, P < 0.01, *P < 0.05.

TABLE VIII

The effect of calcium L-threonate on the dry femur weight, ash weight and calcium content of ovariectomized rats with osteoporosis(X ± SD)

| Group | dry femur weight (mg) | ash (mg) | calcium content(mg/g dry weight) |
|---|---|---|---|
| calcium L-threonate | | | |
| high dosage group | 546.6 ± 22.8** | 332.4 ± 13.0** | 445.7 ± 57.0*** |
| middle dosage group | 553.0 ± 38.1** | 325.3 ± 23.5** | 455.1 ± 66.6*** |
| low dosage group | 517 ± 21.8 | 308.5 ± 11.4* | 387.8 ± 91.9 |
| Caltrate-D group | 509.2 ± 18.2 | 308.4 ± 12.9** | 488.6 ± 92.5*** |
| model-control group | 493.4 ± 28.1 | 282.3 ± 30.5 | 341.9 ± 43.9 |
| normal-control group | 503.2 ± 27.3 | 311.9 ± 17.6** | 368.9 ± 66.6 | note: n = 13, *P < 0.001, P < 0.01 *P < 0.05.

Table VIII showed that feeding the ovariectomized rats with calcium L-threonate chronically could markedly control and inhibit the loss of bone matrix. This made dry femur weight, ash weight and calcium content of rats markedly higher than those of model-control group rats. So, calcium L-threonate could prevent the ovariectomized rats from loss of bone matrix.

(3) Bone Mechanical Characteristics

The biochemical characteristics of femur were evaluated by parameters such as bone strength, tenacity, calcified degree and the work to break a bone. The test results in Table IX showed that P,K,Y and S values of the calcium L-threonate group were markedly increased compared with those of the model-control group. This demonstrated that calcium L-threonate could enhance the strength of femur (P value), increase the calcified degree of bone (K value), raise the tenacity of bone (Y value) and the work to break the bone (S value). Furthermore, this effects of calcium L-threonate were superior to those of Caltrate-D.

TABLE IX

The effect of calcium L-threonate on femur biomechanics of ovariectomized rats with osteoporosis(X ± SD)

| Group | P | K | Y | S |
|---|---|---|---|---|
| calcium L-threonate | | | | |
| high dosage group | 9.6 ± 1.7*** | 2.63 ± 0.52 | 5.9 ± 1.2** | 29.4 ± 10.2*** |
| middle dosage group | 8.5 ± 0.8** | 2.75 ± 0.31* | 5.3 ± 1.4* | 23.2 ± 11.6** |
| low dosage group | 7.9 ± 1.0* | 2.71 ± 0.36 | 4.1 ± 0.7 | 14.0 ± 3.4* |
| Caltrate-D group | 8.6 ± 1.0** | 2.52 ± 0.28 | 5.0 ± 1.2* | 21.2 ± 10.0** |
| model-control group | 6.7 ± 1.2 | 2.35 ± 0.36 | 4.0 ± 1.1 | 11.3 ± 4.7 |
| normal-control group | 8.1 ± 1.2** | 2.57 ± 0.35* | 4.3 ± 0.8 | 16.0 ± 5.4* | note: n = 13, in comparison with model group *P < 0.001, P < 0.01, *P < 0.05.

Test III. Study of the Preventing-Effect of Calcium L-threonate on Castration-Induced Osteoporosis in Male Rats In this test, chemicals were the saine as in test II, animals were male Wistar rats each weighing 150±10 g and were provided by Animal Center of the National Institute for the Identification of Pharmaceuticals and Biological Products, Beijing. The breeding of the rats was the same as in test II.

The pure synthetic low-calcium diet and apparatus used in this test were the same as in test II.

(1) Preparation of castration-induced osteoporosis model

The male rats each weighing 150±10 g were excised of bilateral spermaries and were fed low-calcium diet and offered deionized water for 60 days, thus made a model of osteoporosis.

(2) Method

Seventy of the castrated male rats were divided into groups and tested in the same manner as Test II but the days of administration were 52 days during the 60 days of test.

In this test, the measuring methods for serum Ca, P, AKP levels, the bone mineral density, the length of femur, wet weight, dry weight, ash weight, the calcium content and the biomechanics of femur were all the same as in test II. The following results were obtained.

(1) serum Ca, P, AKP levels

TABLE X

The effect of calcium L-threonate on the serum Ca, P levels of castrated male rate with osteoporosis

| Group | serum Ca(mmol/L) | serum P(mmol/L) |
|---|---|---|
| calcium L-threonate | | |
| high dosage group | 2.17 ± 0.62* | 1.48 ± 0.55* |
| middle dosage group | 2.20 ± 0.60* | 1.78 ± 0.55 |

TABLE X-continued

The effect of calcium L-threonate on the serum Ca, P levels of castrated male rate with osteoporosis

| Group | serum Ca(mmol/L) | serum P(mmol/L) |
|---|---|---|
| low dosage group | 1.97 ± 0.52 | 1.87 ± 0.39 |
| Caltrate-D group | 1.87 ± 0.72 | 1.39 ± 0.48* |
| model group | 1.80 ± 0.37 | 2.03 ± 0.48 |
| normal-control group | 2.40 ± 0.60** | 1.42 ± 0.23* | note: n = 14, in comparison with model group **$P < 0.01$, *$P < 0.05$.

Table X showed that the serum calcium level of rats fed calcium L-threonate was significantly higher than that of model group, which demonstrated that feeding the rats calcium L-threonate long-term alone could prevent and inhibit the disease of low calcium level in blood of rats caused by the shortage of androgen and insufficient uptake of calcium.

(2) serum AKP level

Alkaline phosphatase is an enzyme which exists in osteoblast. When bone suffers impairment, the enzyme's activity is enhanced. The test result in Table XI showed that the serum AKP level of the model group rats was significantly higher than that of the normal-control group rats. This demonstrated that the castration of male rats and low-calcium diet could result in the destruction of bone. In contrast, the serum AKP level of rats fed calcium L-threonate chronically was markedly lower than that of the model group rats. This demonstrated that calcium L-threonate could prevent and inhibit the destruction of bone, retard and reduce the loss of bone, and is superior to caltrate-D.

TABLE XI

The effect of calcium L-threonate on the serum AKP level of castrated male rats with osteoporosis

| Group | AKP level in serum (in Bessey-Loury unit) (U/L) |
|---|---|
| calcium L-threonate | |
| high dosage group | 56.1 ± 6.2*** |
| middle dosage group | 59.2 ± 12.0*** |

TABLE XI-continued

The effect of calcium L-threonate on the serum AKP level of castrated male rats with osteoporosis

| Group | AKP level in serum (in Bessey-Loury unit) (U/L) |
|---|---|
| low dosage group | 88.3 ± 13.7 |
| Caltrate-D group | 75.5 ± 15.2 |
| model group | 96.7 ± 26.4 |
| normal-control group | 59.6 ± 8.0*** | note: n = 14, in comparison with model group ***$P < 0.01$.

(3) The bone mineral density, the length of femur, wet weight, dry weight, ash weight and the calcium content

TABLE XII

The effect of calcium L-threonate on the bone mineral density of castrated male rats with osteoporosis(X ± DS)

| Group | F50(BMC/BW) | F20(BMC/BW) |
|---|---|---|
| calcium L-threonate | | |
| high dosage group | 0.274 ± 0.018*** | 0.327 ± 0.033*** |
| middle dosage group | 0.269 ± 0.019** | 0.308 ± 0.020*** |
| low dosage group | 0.255 ± 0.025* | 0.297 ± 0.037*** |
| Caltrate-D group | 0.263 ± 0.016** | 0.278 ± 0.018*** |
| model-control group | 0.235 ± 0.022 | 0.244 ± 0.025 |
| normal-control group | 0.264 ± 0.018 | 0.294 ± 0.020* | note: in comparison with model group *$P < 0.001$, $P < 0.01$, *$P < 0.05$.

TABLE XIII

The effect of calcium L-threonate on the wet weight, dry weight, ash weight and the calcium content of femur of castrated male rats with osteoporosis(X ± DS)

| Group | length of femur(cm) | wet weight(g) | dry weight(g) | ash weight(mg) | calcium content |
|---|---|---|---|---|---|
| calcium L-threonate | | | | | |
| (1)2.31 g/kg/d | 3.35 ± 0.09* | 747.3 ± 95.2** | 473.4 ± 57.2*** | 278.2 ± 31.8*** | 266.7 ± 15.9** |
| (2)1.54 g/kg/d | 3.34 ± 0.08* | 720.2 ± 69.7** | 458.1 ± 39.1*** | 269.66 ± 23.4** | 268.2 ± 15.8** |
| (3)0.76 g/kg/d | 3.34 ± 0.05* | 688.4 ± 47.4* | 416.7 ± 29.7** | 233.1 ± 19.76** | 267.0 ± 16.1** |
| Caltrate-D group(0.65 g/kg/d) | 3.34 ± 0.11* | 719.6 ± 73.2** | 451.6 ± 42.3*** | 260.6 ± 25.3** | 279.9 ± 13.7*** |
| model group (0.00 g/kg/d) | 3.26 ± 0.09 | 638.3 ± 57.6 | 360.0 ± 32.1 | 187.5 ± 18.0 | 245.1 ± 25.7 |
| normal-control group | 3.34 ± 0.06* | 779.6 ± 75.9* | 490.3 ± 41.8 | 283.0 ± 21.5 | 293.8 ± 28.0* | note: n = 14, in comparison with model group, *$P < 0.001$, $P < 0.01$, *$P < 0.05$.

Table XII showed that the bone mineral density of rats fed with calcium L-threonate alone for long time was significantly higher than that of model group, wherein the beneficial effect of calcium L-threonate on increase of bone mineral density related with dosages. Further, the BMD values of calcium L-threonate groups are higher than those of normal control group and Caltrate-D group.

Table XIII showed that feeding rats calcium L-threonate chronically could effectively control and retard the loss of bone, maintain the normal development of femur, prevent and cure the loss of bone matrix caused by castration and thus provide a markedly higher femur length, wet weight, dry weight, ash weight and calcium content than those of the model group rats.

(4) Measurement of the femur biomechanics

Table XIV showed that the P,K,S values of the calcium L-threonate group rats markedly increased in contrast to those of the model group rats. This demonstrated that calcium L-threonate could raise the strength of femur (P value), the calcification of bone (K value) and the work to break the bone (S value).

TABLE XIV

The effect of calcium L-threonate on the femur biomechanics of castrated male rats with osteoporosis

| Group | P | K | Y | S |
|---|---|---|---|---|
| calcium L-threonate | | | | |
| high dosage group | 9.3 ± 0.9*** | 2.52 ± 0.22*** | 6.3 ± 1.0* | 28.7 ± 7.8 |
| middle dosage group | 8.7 ± 1.2** | 2.27 ± 0.42** | 6.6 ± 1.1 | 28.3 ± 9.4 |
| low dosage group | 7.6 ± 1.1* | 2.05 ± 0.25* | 7.3 ± 1.6 | 29.7 ± 9.2 |
| Caltrate-D group | 8.5 ± 0.9** | 2.33 ± 0.27** | 7.1 ± 1.6 | 32.4 ± 11.0* |
| model-control | 5.2 ± 1.1 | 1.50 ± 0.26 | 8.0 ± 1.2 | 24.5 ± 7.5 |
| normal-control group | 8.7 ± 1.2 | 2.41 ± 0.31 | 7.0 ± 1.2 | 33.7 ± 9.9** | note: n = 13, in comparison with model group, *P < 0.001, P < 0.01, *P < 0.05.

Test XV. The Study of Calcium L-threonate on Preventing Rickets in Younger Mice

1. Animals and Their breeding

The weanling mice of Kunming species, aged 20–22 days, each weighing 10–12 g were provided by Animal Center of the National Institute for the Identification of Pharmaceutical and Biological Products, Beijing. The mice were bred for 60 days under conditions of avoiding light around-the-clock, at a temperature of 20–25° C. and a relative humidity of 40–60% while the normal-control group mice were fed ordinary diet and water and were placed in non-dark room.

The low-calcium diet used in this test was the same as that in Test II but $V_D$ in the vitamin mixture was replaced by glucose.

2. Preparation of ricket model

Some weanling mice were placed in dark room and fed $V_D$-deficient low-calcium diet and drunk de-ionized water for 60 days, thus a ricket model of baby mice was prepared. While other weanling mice were placed in non-dark room and fed ordinary diet and drunk tap water for 60 days, these mice were established as normal-control group.

3. Experimental Results (1) The effect of calcium L-threonate on serum Ca, P, AKP levels: Table XV showed that serum Ca levels of the groups of high and low dosage of calcium L-threonate were approximate to that of the normal-control group but were much higher than those of the model group while serum AKP levels were much lower than those of the model group. This demonstrated that administering calcium L-threonate could prevent and retard the decrease of serum Ca level, inhibit resorption of bone, and reduce AKP level.

TABLE XV

The effect of calcium L-threonate on serum Ca, P, AKP, Tr-ACP levels of rickets-mice

| Group | Ca(mmol/L) | AKP(in Bessey-Loury unit)(U/L) | P(mmol/L) |
|---|---|---|---|
| calcium L-threonate | | | |
| 2.31 g(300 mg calcium element) | 2.17 ± 0.82** | 43.1 ± 14*** | 1.35 ± 0.34*** |

TABLE XV-continued

The effect of calcium L-threonate on serum Ca, P, AKP, Tr-ACP levels of rickets-mice

| Group | Ca(mmol/L) | AKP(in Bessey-Loury unit)(U/L) | P(mmol/L) |
|---|---|---|---|
| 1.54 g(200 mg calcium element) | 2.33 ± 0.82** | 59.3 ± 14*** | 1.52 ± 0.45*** |
| calcium gluconate 3.37 g(300 mg calcium element) | 2.37 ± 0.97** | 46.6 ± 13*** | 1.71 ± 0.45** |
| model group (0.00 g/kg/d) | 1.55 ± 0.42 | 101 ± 34 | 2.23 ± 0.52 |
| normal-control group(0.00 g/kg/d) | 2.35 ± 0.85 | 55.4 ± 12 | 1.55 ± 0.45** | note: n = 18, in comparison with model group, *P < 0.001, P < 0.01.

(2) The effect of calcium L-threonate on the dry weight, ash weight and the total calcium content of the femur. Data in Table XVI showed that the body weights of animals were not markedly affected by the administration of calcium L-threonate, but the dry femur weight, ash weight and the total calcium content of both the high and low dosage of calcium L-threonate groups were markedly higher than those of the model group and were approximate to those of the normal-control group. This demonstrated that supplementing calcium L-threonate chronically could prevent and inhibit the loss of bone matrix and prevent rickets. Additionally, Table XVI showed that Ca deposited in femur of calcium L-threonate was much higher than that of calcium gluconate (P<0.05).

TABLE XVI

The effect of calcium L-threonate on the dry weight, ash weight and the total calcium content of femur of rickets-mice(X ± SD)

| Group | body weight(g) | dry weight of femur(g) | ash weight(mg) | total calcium content(mg) |
| --- | --- | --- | --- | --- |
| calcium L-threonate | | | | |
| 231 g(300 mg calcium element) | 37.3 ± 4.3 | 0.131 ± 0.013* | 74.73 ± 12.31*** | 38.90 ± 13.78**Δ |
| 1.54 g(200 mg calcium element) | 36.5 ± 4.7 | 0.121 ± 0.010* | 69.44 ± 6.62** | 36.23 ± 7.53**Δ |
| calcium gluconate 3.37 g(300 mg calcium element) | 36.1 ± 5.1 | 0.122 ± 0.019 | 70.76 ± 10.18** | 30.23 ± 5.23** |
| model group (0.00 g/kg/d) | 37.2 ± 4.6 | 0.099 ± 0.014 | 46.62 ± 9.38 | 24.81 ± 4.36 |
| normal-control (0.00 g/kg/d) | 35.3 ± 5.5 | 0.130 ± 0.011* | 70.01 ± 6.82*** | 37.01 ± 8.32 | note: n = 18, in comparison with model group, *$P < 0.001$, $P < 0.01$; in comparison with the calcium gluconate group, $^\Delta P < 0.05$.

(3) The analysis of the effect of calcium L-threonate on the strength of tibia in rickets-mice. The results of three-point bending test of tibia in table XVII showed that the breaking forces for the calcium L-threonate group and the calcium gluconate group were significantly higher than those for the model group and were comparable with those for the normal-control group. This demonstrated that supplementing calcium L-threonate chronically could reinforce the anti-breaking strength of tibia, inhibit and prevent rickets.

TABLE XVII

The effect of calcium L-threonate on tibia strength of rickets-mice(X ± SD)

| Group | breaking force(kg) |
| --- | --- |
| calcium L-threonate | |
| 2.31 g(300 mg calcium element) | 1.59 ± 0.27(18)** |
| 1.54 g(200 mg calcium element) | 1.49 ± 0.38(15)* |
| calcium gluconate 3.37 g(300 mg calcium element) | 1.54 ± 0.35(15)* |
| model group (0.00 g/kg/d) | 1.12 ± 0.37(17) |
| normal-control group(0.00 g/kg/d) | 1.48 ± 0.34(16)* | note: in comparison with model group **$P < 0.01$, *$P < 0.05$.

Test V. The Study on the Enhancing Effect of Calcium L-threonate on the Bone Mineral Density of Preschool Children 1. subjects Seventy 3–6 years old healthy children whose bone mineral density were medium-lower at a central kindergarten in the suburban county of Beijing were selected as subjects, wherein there are 13 boys and 57 girls. All were healthy children who didn't have any metabolic diseases, liver or kidney diseases, bone wounds and abnormal diseases.

2. Grouping

Seventy children were randomly divided into four groups which were observed for 3 months. Double blind method was employed during the observation. Every person was administered calcium preparation or placebo twice a day in a dosage of 1 bag each time. Group I (test group I) were administered 2 bags of calcium L-threonate every day wherein each bag contained 200 mg element calcium. Group II (test group II) were administered 2 bags of calcium L-threonate every day wherein each bag contained 150 mg element calcium. Group III (calcium carbonate group) were administered 2 bags of calcium carbonate every day wherein each bag contained 150 mg element calcium. Group IV, established as blank-control group, was administered placebo which didn't contain calcium. All the above oral preparations were provided by Beijing Juneng Asian-Pacific Life Science Research Center.

3. Methods (1) Bone mineral density was measured before the test and 1.5 months and 3 months later after the administration of Ca supplements.

(2) Measurement of BMD.

The bone mineral density of radius in non-preferred hand was measured at the ⅓ point near the farther-end by a Model BMD400 Single-Photon absorptiometry produced conjointly by Institute of Atomic Energy, Ministry of Nuclear Industry, China and Institute of Broadcasting, Beijing, to obtain mean mineral bone density (BMD, $g/cm^2$). Each point was scanned twice with a scanning speed of 0.5 mm/sec.

(3) Data processing.

All data was analyzed with a SAS statistical software package.

4. Results (1) There was no significant difference among BMDs of the four groups of children when the children were divided into groups. From then on, the test of calcium supplementing began, the results were shown in Table XVIII.

TABLE XVIII

Variations of the bone mineral density of four groups of
children before and after the test(g/cm$^2$)

| group | reciprocal | before test | 1.5 month | 3 month |
|---|---|---|---|---|
| I | 20 | 0.362 ± 0.026 | 0.414 ± 0.027*,a | 0.460 ± 0.020##,a |
| II | 16 | 0.379 ± 0.028 | 0.424 ± 0.038*,a | 0.467 ± 0.027##,a |
| III | 18 | 0.369 ± 0.031 | 0.385 ± 0.028*,b | 0.412 ± 0.020##,b |
| IV | 16 | 0.358 ± 0.028 | 0.375 ± 0.020*,b | 0.385 ± 0.038*,c | note: compared with before test *p < 0.05, compared between 3 month and 1.5 month #p < 0.05 with different superscript label (a, b, c) p < 0.05

Table XVIII showed that BMDs of the four groups of children were all markedly enhanced after 1.5 and 3 months of observations compared with those before the test (P<0.05). Furthermore, apart from that there was no significant difference between BMDs of the blank-control group (IV) in 1.5 months and 3 months, BMDs of the other three groups of children in 3 months were all markedly higher than that in 1.5 months (P<0.05). By comparing BMDs of the four groups of children in 1.5 months and 3 months, it could be found that there was no significant difference between group I and II of calcium L-threonate treatment (P>0.05), but BMDs of group I and II of calcium L-threonate were all markedly higher than those of the calcium carbonate group and those of the blank-control group (P<0.05). BMD of the calcium carbonate group was markedly higher than those of the blank-control group only in 3 months (P<0.05) while there was no significant difference of BMDs between these two groups in 1.5 months.

(2) The extent of BMDs' increase in four groups of children were shown in Table XIX.

TABLE XIX

Extent of BMDs' increase in four groups of children (%)

| Group | 1.5 months | 3 months |
|---|---|---|
| I | 14.36 | 25.41 |
| II | 11.87 | 23.22 |
| III | 4.37 | 11.65 |
| IV | 4.75 | 7.26 |

Table XIX showed that the extent of BMDs' increase in the calcium L-threonate group was markedly higher than that in the calcium carbonate group and that in the blank-control group, and was about twice as that in the calcium carbonate group.

(3) The percentages of children in the four groups whose BMDs arrived the normal range of value after the test on the administration of calcium were shown in Table XX.

TABLE XX

The percentages of children in the four groups whose BMDs
reached the normal range of value after the test on
the administration of calcium (%).

| group | 1.5 months | 3 months |
|---|---|---|
| I | 10 | 70** |
| II | 12.5 | 75** |
| III | 0 | 16.7 |
| IV | 0 | 0 |

Note: in comparison with that of the calcium carbonate group and that of the blank-control group, **P < 0.01.

Table XX showed that there were about ⅔ of the children in the calcium L-threonate group whose BMD reached the normal level after 3 months of Ca-administration while in the calcium carbonate group, there were only ⅙ of the children whose BMD reached the normal level; while in the blank-control group, although all BMDs of the children markedly increased, they were still under normal levels.

Test VI Study of the Effect of Calcium L-threonate on Curing Babies of Rickets 1. subjects Fourty rickets-babies at the age of 3–10 months were randomly divided into 2 groups of 20 babies each. Test group I, namely the calcium L-threonate group, were administered orally calcium L-threonate twice a day in a dosage of one bag each time. Test group II, namely the calcium carbonate group, were administered orally calcium carbonate twice a day in a dosage of one bag each time. Each bag of the two kind of calcium preparations contained the same amount of element calcium, namely 150 mg element calcium. Both calcium L-threonate and calcium carbonate were provided by Beijing Juneng Asia-Pacific Life Science Research Center.

2. Methods

The selection of rickets-babies and treating results of administrating calcium supplements were evaluated as a whole on both basis of clinic symptoms and serum biochemical examinations.

(1) Clinic symptoms mainly included the normal symptoms of rickets-babies such as night-sweat, pillow-bald, craniomalacia, etc.

(2) Biochemical examinations of blood. Venous blood of rickets-baby was sampled before and after the beginning of test and serum Ca, P and AKP level were measured and the product of [Ca]×[P] was calculated. As a biochemical examination, colorimetric assay was performed by using USA model 7170 Full-Automatic Biochemical Analyzer.

(3) Data processing: All data was statistically analyzed using the method of direct calculation of probability, grouping t-test and pairing t-test.

3. Result (1) improvement of rickets-babies' symptoms

All of the rickets-babies were randomly divided into two groups, wherein the distributions of the said three symptoms in the two groups were the same and there was no significant difference (P>0.05). At the second week and the fourth week after the administration of Ca supplements, the 40 rickets-babies of the two groups were examined of rickets symptoms respectively. The results (table XXI) showed that at the second week, symptoms of rickets-babies in the calcium L-threonate group were improved by 62.5% while that in the calcium carbonate group was only by 11.5%. At the fourth week (table XXII), all symptoms of rickets-babies in the calcium L-threonate group were significantly improved 100% while those in the calcium carbonate group were only by 57.6%.

TABLE XXI

Symptom examples of rickets babies in the two groups before and after the beginning of test (two weeks)

| | calcium L-threonate group | | calcium carbonate group | |
|---|---|---|---|---|
| symptom | before the test | after the beginning of test | before the test | after the beginning of test |
| night-sweat | 12 | 0 | 13 | 10 |
| pillow-bald | 9 | 7 | 9 | 9 |
| craniomalacia | 3 | 2 | 4 | 4 |
| total symptom improvement (%) | | 62.5 | | 11.5 |

TABLE XXII

Symptom examples of rickets-babies in the two groups before and after the beginning of test (four weeks)

| | calcium L-threonate group | | calcium carbonate group | |
|---|---|---|---|---|
| symptom | before the test | after the beginning of test | before the test | after the beginning of test |
| night-sweat | 12 | 0 | 13 | 3 |
| pillow-bald | 9 | 0 | 9 | 5 |
| craniomalacia | 3 | 0 | 4 | 3 |
| total symptom improvement (%) | | 100 | | 57.6 |

(2) Variations in serum biochemical indexes

Considering the difficulty in sampling blood from rickets-babies during the test operation, blood sampling was not performed at the second week after the beginning of the test. Blood sampling was only performed before the test and at the fourth week after the beginning of the test. The sampled blood was measured and the results were shown in Table XXIII.

TABLE XXIII

Biochemical examination results of two groups of rickets-babies before and after the beginning of test (X ± SD)

| | calcium L-threonate | | calcium carbonate | | average |
|---|---|---|---|---|---|
| indexes | before the test | after the beginning of test | before the test | after the beginning of test | normal value |
| serum Ca | 10.49 ± 0.39 | 10.65 ± 0.35 | 10.51 ± 0.47 | 10.55 ± 0.42 | 10–12(2) |
| serum P | 3.19 ± 0.25 | 4.50 ± 0.26**$^\Delta$ | 3.12 ± 0.20 | 3.90 ± 0.52** | 4–6 |
| AKP | 235.95 ± 7.89 | 203.75 ± 11.46**$^\Delta$ | 235.25 ± 7.37 | 225.25 ± 22.93* | 106–213 |
| [Ca] × [P] | 33.4 ± 2.47 | 47.34 ± 3.15$^\Delta$ | 33.83 ± 2.17 | 43.19 ± 5.22 | 40 | note: n = compared between before and after test in the same group *p < 0.05 **p < 0.01; compared with calcium carbonate group Δp < 0.01

Table XXIII showed that there was no significant difference between the two groups of rickets-babies concerning the above four indexes before the test. This demonstrated that the blood biochemical results of the two randomly-divided groups of rickets-babies were also identical. There was no significant variation in the serum Ca levels of the two groups of rickets-babies before and after the test (P>0.05). Also, the average serum Ca levels were all in normal range. As for the other three indexes, according to the pairing t-test before and after the test of the two groups of babies, except that P value of AKP in the calcium carbonate group was lower than 0.05, the other P value was lower than 0.01, that is to say that the difference was highly significant. There was highly significant difference (P<0.01) between the results of serum P,AKP and [Ca]×[P] of the two groups after the test had begun.

In the calcium carbonate group, although there was highly significant difference (P<0.01) between the results of serum P, AKP and [Ca]×[P] before the test and those after the test, serum P and AKP after test didn't reach the normal range of value.

TABLE XXIV

The percentage in which the blood biochemical examination indexes of two groups of rickets-babies reached the normal range of value after four weeks of Ca-supplementing (%)

| group | serum P | AKP | [Ca] × [P] |
|---|---|---|---|
| calcium L-threonate group | 100** | 90** | 100* |
| calcium carbonate group | 60 | 30 | 70 | note: *p < 0.05 **p < 0.01

Using the method of direct computation of probability, it was found that there was highly significant difference (P<0.01) between the results of serum P, AKP of the two groups and the markedly difference of [Ca]×[P] between the two groups (P<0.05).

On the basis of the test and study with calcium carbonate as a constrast, it was found that calcium L-threonate could markedly and rapidly improve symptoms of rickets, in which two weeks of Ca L-threonate administrating could make 62% rickets-babies free of symptoms while in case of calcium carbonate, only 50% rickets-babies could free of symptoms. The blood biochemical examinations also showed that four weeks of calcium L-threonate-administrating could markedly improve the blood biochemical indexes of all rickets-babies and raise the indexes to the normal range of value while in the case of calcium carbonate, although the blood biochemical indexes of rickets-babies were also improved, the serum P,AKP didn't reach their normal range.

What is claimed is:

1. A method for treating, preventing and/or inhibiting osteoprosis, which comprises administering an effective amount of calcium L-threonate to individuals having an insufficient uptake of calcium or patients suffered from osteoporosis.

2. A method according to claim 1, wherein the amount of calcium L-threonate is in the range of 0.5–12 g a day, preferably in the range of 2–10.6 g a day, more preferably in the range of 3–7 g a day on the basis of an adult.

3. A method for treating, preventing and/or inhibiting rickets, which comprises administering an effective amount of calcium L-threonate to individuals having an insufficient uptake of calcium or patients suffering from rickets.

4. A method according to claim 3, wherein the amount of calcium L-threonate is in the range of 0.5–12 g a day, preferably in the range of 2–10.6 g a day, more preferably in the range of 3–7 g a day on the basis of an adult.

* * * * *